United States Patent [19]

Shackelford

[11] Patent Number: 5,209,108

[45] Date of Patent: May 11, 1993

[54] RHEOLOGICAL TEST APPARATUS AND METHOD USING A HELICAL SCREW RHEOMETER

[75] Inventor: Donald W. Shackelford, Duncan, Okla.

[73] Assignee: Halliburton Company, Duncan, Okla.

[21] Appl. No.: 493,589

[22] Filed: Mar. 13, 1990

[51] Int. Cl.[5] ............................................. G01N 11/14
[52] U.S. Cl. .................................................... 73/54.28
[58] Field of Search ................................. 73/54, 56, 59

[56] References Cited

U.S. PATENT DOCUMENTS

| | | |
|---|---|---|
| 1,810,992 | 6/1931 | Dallwitz-Wegner . |
| 3,298,190 | 1/1967 | Harker ..................................... 73/59 |
| 3,504,529 | 4/1970 | Hirs ......................................... 73/54 |
| 4,077,251 | 3/1978 | Winter ..................................... 73/59 |
| 4,700,567 | 10/1987 | Frey et al. .............................. 73/151 |
| 4,878,378 | 11/1989 | Harada . |

FOREIGN PATENT DOCUMENTS 711851 3/1986 United Kingdom .

OTHER PUBLICATIONS

Sandia National Laboratories memorandum dated Mar. 30, 1984, titled "Stability of Flow in Helical Screw Rheometer".
Society of Petroleum Engineers Paper No. SPE 18213 entitled "Helical Screw Rheometer: A New Tool For Stimulation FLuid Evaluation" by D. L. Lord of Halliburton Services, published for conference held Oct. 2-15, 1988.
Society of Petroleum Engineers Paper No. SPE 19734 entitled "Real-Time Fracturing Fluid Rheology Measurements with a Helical Screw Rheometer", by D. L. Lord and Donald W. Shackleford of Halliburton Services, published for conference held on Oct. 8-11, 1989.

*Primary Examiner*—Jerry W. Myracle
*Attorney, Agent, or Firm*—James R. Duzan; Neal R. Kennedy

[57] ABSTRACT

A rheological test apparatus and method using a helical screw rheometer. The screw in the rheometer is driven by a hydraulic motor controlled by a proportioning valve. A pressure transducer provides a pressure signal at the outlet of the rheometer, and a solenoid valve is used to close the outlet downstream from the pressure transducer. In a test, fluid is flowed into the rheometer. With the screw stopped and the discharge closed, a static pressure is measured by the pressure transducer, and a computer means resets this to a zero reference value. The screw in the rheometer is then rotated at a constant speed with the discharge closed, and the dynamic pressure at the outlet is measured by the pressure transducer. Because the static pressure was zeroed, the dynamic pressure value is substantially equal to the differential pressure across the rheometer. The test is repeated for different speeds. In an alternate embodiment, the speed of the rheometer is varied over a period of time, and a series of dynamic pressure values are obtained which are substantially equal to a series of differential pressures across the rheometer for the corresponding speeds in the speed range. In both methods, the computer calculates, in response to the differential pressure values and speeds, the n' and k' parameters of a shear rate versus shear stress relationship of the fluid. Using these parameters, predictions of friction pressure loss and bottom hole treating pressure during a well fracturing treatment may be generated.

16 Claims, 4 Drawing Sheets

RHEOLOGICAL TEST APPARATUS AND METHOD USING A HELICAL SCREW RHEOMETER

BACKGROUND OF THE INVENTION

1. Field Of The Invention

The present invention relates to the rheological testing to measure fluid properties such as for controlling the base gel quality during well fracturing treatments, and more particularly, to the measurement of these fluid properties using a helical screw rheometer controlled by a computer means.

2. Description Of The Prior Art

Once an oil or gas well is drilled, it is sometimes necessary to fracture a formation to improve the flowability of the hydrocarbons trapped in the formation. To perform a fracturing job, specialized fracturing fluids suitable for the specific job are blended. The fracturing fluids are delivered to the well site by blending selected chemicals into a base gel, the characteristics of which can be controlled based upon rheological properties as determined from real-time measurements taken, for example, through the use of a laminar flow rheology loop. Such measurements can also be used for predicting friction pressure loss and bottom hole treating pressures that are likely to occur when the blended fluid is pumped down hole during the fracturing process. Such control and prediction abilities enhance the chances of obtaining a good result from the fracturing job under way, and the information obtained therefrom is helpful in designing other blends for subsequent jobs.

One technique for obtaining such control and prediction abilities is based upon the shear rate versus shear stress relationship applicable to the particular base gel being used. This relationship can be determined by monitoring differential pressures on various lengths and diameters of the flowing base gel. Measurements of such differential pressures correlate to points on a graphical representation of the particular shear rate versus shear stress relationship. For example, a least squares fit calculation can be used with the differential pressure measurements to compute a straight line having a slope representing the n' value and having a unity intercept representing the k' value for the log of the shear rate versus the log of the shear stress relationship. These values are used by a computer for correlating the turbulent flow in pipes of other diameters and for providing other suitable information on a realtime basis. The mathematical relationships of this technique are known in the art.

The foregoing technique of using differential pressure measurements to develop a shear rate versus shear stress relationship can be correlated into useful, real-time information by which the quality of a gel can be controlled and by which predictions of downhole phenomena can be made has been implemented by a portable laminar flow rheology skid developed and used by Halliburton Services prior to October, 1984. This skid is transportable by a vehicle dedicated to that function, such as a pickup truck, but is electrically connectable to a COMPUVAN ® testing vehicle for providing the differential pressure information to computers in the testing vehicle. The computers generate the correlations and predictions based on the differential pressure information.

In operation, this prior skid has been used with a blending system that includes frac tanks containing the base gel, a blender tub, a suction pump for pumping the gel from the frac tanks to the blender tub, a differential pump for pumping the blend from the tub for subsequent high pressure pumping, by other pumps, into the well. Additives can be blended into the base gel through application into the tub or along the flow path as known in the art. The prior laminar flow rheology loop has an inlet connected to receive a portion of the clean base gel tapped from the flow between the suction pump and the tub. The rheology loop has an outlet through which the tapped portion flows into the tub.

The tapped flow circulates through at least part of the loop which comprises four test pipe sections having different diameters (e.g., nominal inner diameters of ⅜ inch, ½ inch, ¾ inch and 1 inch). A respective differential pressure transducer and two respective pressure taps are used to measure the pressure drop over a specified length in each pipe section. To increase the range of gel viscosities than can be accommodated in this flow loop, only three test pipe sections are used by the computer program at any one time (in this embodiment, either the three larger pipe sections or the three smaller pipe sections). If a relatively thin fluid is being used, for example, then lower flow rates or larger pipes will keep the flow laminar.

In this prior rheology loop, the flow rate of the base gel being circulated through the loop must also be controlled and measured. The flow rate is controlled by a 1-inch ball valve, and the flow rate is measured in one of two different ways, depending upon the type of gel being circulated. If an aqueous (conductive) gel is measured through the loop, a magnetic flow meter measures the flow rate. If a non-aqueous (non-conductive) gel is circulated, a standard turbine flow meter measures the flow rate.

The prior skid also includes a pH probe and temperature probe placed in the flow stream to monitor these characteristics of the base gel.

The prior skid also includes a bypass valve so that the ⅜-inch test pipe section can be removed from the flow stream. This is used not only to select between which set of three test pipe sections is to be used, but also to bypass the smallest pipe should the outlet pressure of the blender tub become marginal whereby such bypassing decreases the back pressure that the laminar flow loop creates in the portion of the flow taken from the blender tub.

Although this prior skid functions satisfactorily, an improved rheology test system has been constructed so that a rheology flow loop skid thereof can be conveniently and readily transported on a complementally constructed vehicle also capable of carrying the computational equipment needed to perform the necessary calculations. This prior art apparatus for measuring rheological properties, disclosed in U. S. Pat. No. 4,700,467 to Frey et al. and assigned to the assignee of the present invention, provides a skid-mounted laminar flow rheology loop which is more compact and lighter in weight than the previous rheology skid so that it can be carried on a complementally constructed test vehicle also carrying computational equipment forming another part of the overall system.

The apparatus of U.S. Pat. No. 4,700,567 provides a transportable rheology test system for generating, at the location of a well, predictions of friction pressure loss in bottom hole treating pressure during a fracturing system being performed on the well. The system comprises a self-propelled vehicle for moving the system to a well site, computer means mounted in the vehicle for calculating, in response to differential pressure values, n' and k' parameters of a shear rate versus shear stress relationship of a flowing substance, from which parameters the predictions are generated. This apparatus further comprises rheology loop means for detecting a plurality of differential pressure values along a plurality of lengths of a fluid flowing therethrough and for providing to the computer means signals representing the plurality of differential pressure values. The rheology flow loop means includes a base and a helical pipe assembly mounted on the base.

The apparatus of U.S. Pat. No. 4,700,567 performs satisfactorily, but requires the rheology flow loop described as well as a plurality of differential pressure gauges associated therewith.

There is, accordingly, a need for rheology test equipment which eliminates much of this piping and simplifies the number of pressure connections. The present invention meets this need by substituting a helical screw rheometer for the previous rheology loop and uses only one pressure transducer located at the outlet of the rheometer.

Generally, the helical screw rheometer is a known device for measuring fluid properties and was developed by Sandia National Laboratories, originally for on-line measurements of slurries in coal liquefaction processes. The accuracy of helical screw rheometers and the ease with which they may be used to determine fluid properties makes them desirable for use at a well. However, prior helical screw rheometers have essentially been laboratory devices, and there is a need for a field version, particularly one designed to control base gel quality during well fracturing treatments. The present invention addresses this need by providing a field helical screw rheometer which is controlled by a computer means.

SUMMARY OF THE INVENTION

The rheology test apparatus of the present invention may be used in determining fluid properties of base gels for well fracturing operations. The apparatus generally comprises a helical screw rheometer with a housing and a screw disposed in the housing, a prime mover for providing relative rotation between the housing and screw, speed control means for controlling a speed of the prime mover, valve means for closing an outlet of the helical screw rheometer, and pressure sensing means for sensing an outlet pressure of the helical screw rheometer when the outlet is closed and in response to a speed of the prime mover. The housing and screw of the helical screw rheometer are relatively rotatable. In the preferred embodiment, the screw is rotatable within the housing, and the screw has a substantially helical thread thereon which is in close relationship to a bore in the housing. The apparatus further comprises speed sensing means for measuring a speed of the prime mover and thus the speed of the rheometer. The valve means is preferably disposed downstream of the pressure sensing means.

In the preferred embodiment, the apparatus further comprises computer means for receiving a signal from the pressure sensing means and a signal from the speed sensing means. The computer means is further used for controlling the speed controlling means and for actuating the valve means for opening and closing the outlet of the rheometer. The computer means also comprises means for calculating an intermediate speed during a series of tests in response to preselected first and last speeds. The computer means additional comprises means for calculating, in response to the pressure sensing means and the speed sensing means, n' and k' parameters of a log of shear rate versus log of shear stress relationship of a fluid in the helical screw rheometer. These parameters may be used for generating predictions of friction pressure loss in bottom hole treating pressure during a fracturing treatment and for controlling the quality of the base gel during the treatments.

The computer means comprises means for resetting a pressure measurement to zero after measuring a static pressure in the helical screw rheometer so that a subsequent measurement of a dynamic pressure in the helical screw rheometer is substantially equal to a differential pressure thereacross. In this way, differential pressure gauges and their associated complex tubing connections are not necessary.

In the preferred embodiment, the prime mover is a hydraulic motor, and the speed control means is a hydraulic proportional valve connected to the hydraulic motor.

The invention also consists of a method of rheological testing comprising the steps of: (a) flowing a fluid into a helical screw rheometer, (b) closing an outlet of the helical screw rheometer, (c) rotating a screw in the helical screw rheometer at a substantially constant speed for a predetermined time period, (d) measuring a differential pressure across the helical screw rheometer, (e) repeating steps (c) and (d) for another substantially constant speed of the helical screw rheometer, and (f) calculating, in response to the differential pressure values and speeds, n' and k' parameters of a log of shear rate versus log of shear stress relationship of the fluid. Preferably, a computer means is used for carrying out step (f). The method further comprises using the computer means for selecting an intermediate speed of the rheometer in a plurality of tests in response to preselected first and last speeds of said tests.

In the preferred embodiment of this method, step (d) of measuring a differential pressure comprises stopping the screw in the helical screw rheometer, measuring a pressure at an outlet of the helical screw rheometer to obtain a static pressure value, resetting the static pressure value to zero, rotating the screw at the constant speed, and measuring a pressure at the outlet of the rheometer to obtain a dynamic pressure value which is thus substantially equal to a differential pressure across the rheometer. Preferably, the computer means is used for resetting the static pressure value to zero, thus providing an "auto-zero" feature.

The invention further consists of an alternate method of rheological testing comprising the steps of: (a) flowing a fluid into a helical screw rheometer, (b) closing an outlet of the helical screw rheometer, (c) rotating a screw in the helical screw rheometer and varying the speed thereof over a speed range for a period of time, (d) periodically measuring a differential pressure across the helical screw rheometer at different speeds over the speed range, and (e) calculating, in response to the differential pressure values and speeds, n' and k' parameters of a shear rate versus shear stress relationship of the fluid. Preferably, a computer means is used for carrying out step (e). The speed range may be preselected or determined by the computer means, and the time intervals between measurements of differential pressure may be preselected or determined by the computer means.

In the preferred embodiment of this alternate method, the speed of the helical screw rheometer is gradually increased over the speed range. Further, step (d) of periodically measuring a differential pressure comprises, prior to varying the speed, measuring a pressure at an outlet of the helical screw rheometer with the screw in the helical screw rheometer stopped to obtain a static pressure value, resetting the static pressure value to zero, rotating the screw over the speed range, and periodically measuring a pressure at the outlet of the helical screw rheometer to obtain a series of dynamic pressure values which is thus substantially equal to a series of differential pressures across the rheometer for the corresponding speeds. Preferably, the computer means is used for resetting the static pressure value to zero, thus again providing an "auto-zero" feature.

It is an important object of the present invention to provide a method and apparatus for measuring fluid proper ties to control the base gel quality during well fracturing treatments using a helical screw rheometer.

It is a further object of the invention to provide such a system with a helical screw rheometer which is computer controlled.

Another object of the invention is to provide a method and apparatus of measuring fluid properties which has an auto-zero feature, thereby needing only one pressure transducer.

Additional objects and advantages of the invention will become apparent as the following detailed description of the preferred embodiment is read in conjunction with the drawings which illustrate such embodiment.

DESCRIPTION OF THE PREFERRED EMBODIMENT

Figure 1:
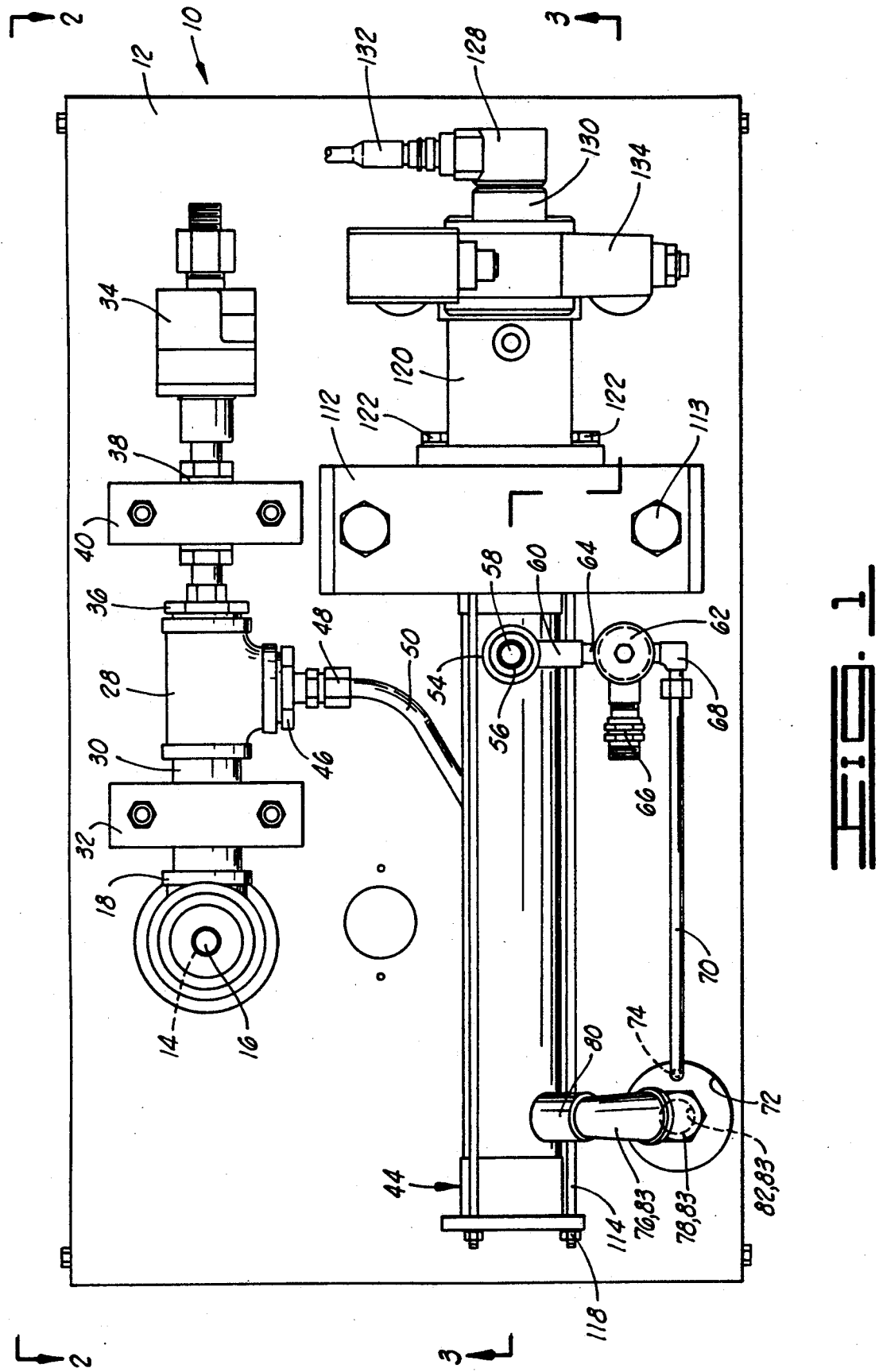
FIG. 1 is a plan view of the rheology test apparatus of the present invention including a helical screw rheometer.
Figure 2:
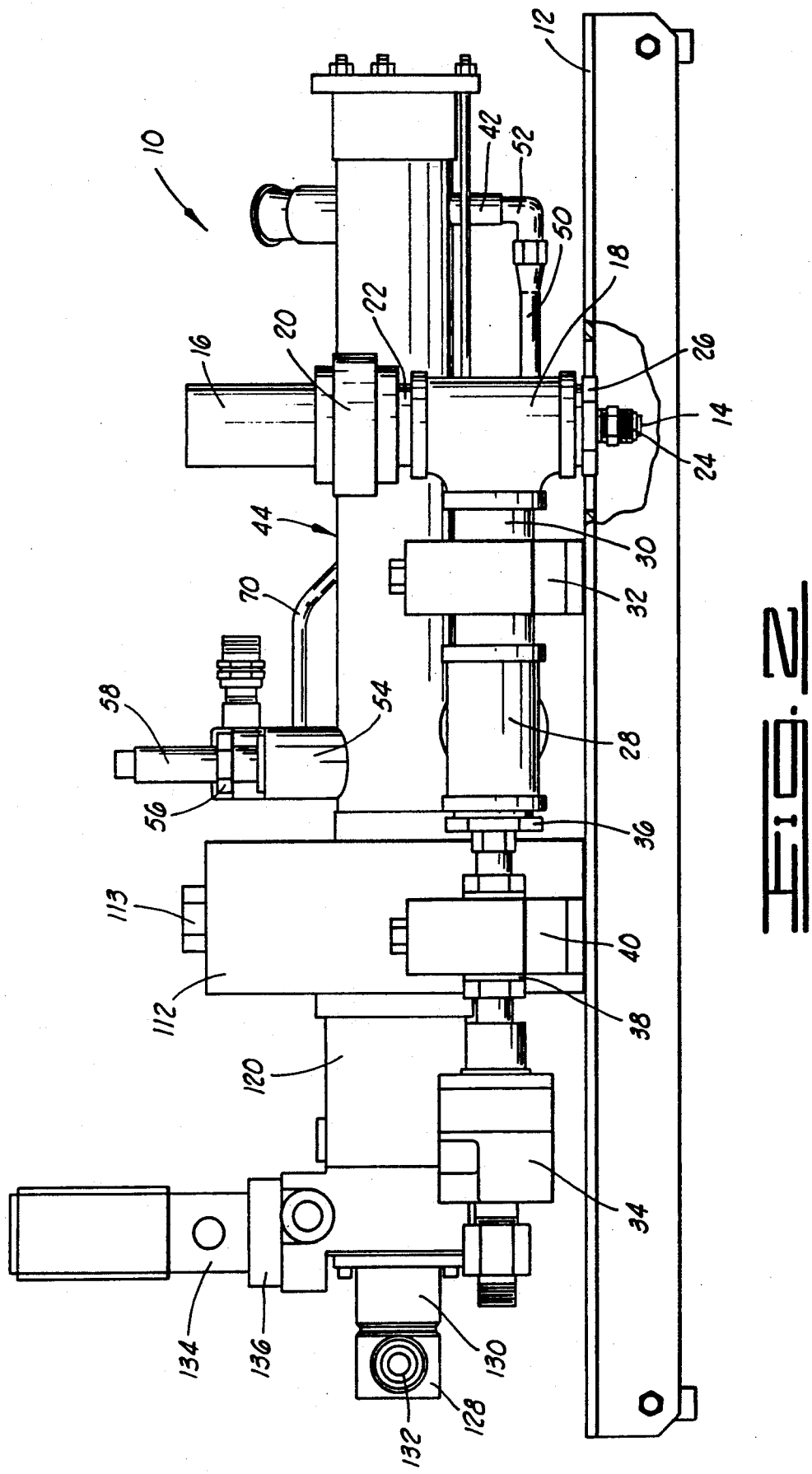
FIG. 2 is a side view of the apparatus taken along lines 2—2 in FIG. 1.

Referring now to the drawings, and more particularly to FIGS. 1 and 2, the rheology test apparatus of the present invention is shown and generally designated by the numeral 10. The various components of apparatus 10 are positioned on a frame 12, although it is not intended that the invention be limited to the particular configuration illustrated.

Fluid enters apparatus 10 through a fluid inlet 14 adjacent to an inlet pH sensor 16 which sensor is connected to a first tee 18 by a union 20 and a nipple 22. Inlet 14 is provided by an adapter 24 and bushing 26 installed in first tee 18.

First tee 18 is connected to the run of a second tee 28 by a tube 30. Tube 30 is supported on frame 12 by a bracket 32.

The other side of the run of second tee 28 is connected to a temperature transmitter 34 by a bushing 36 and a hose 38. Hose 38 is supported on frame 12 by a bracket 40.

The cross portion of second tee 28 is connected to inlet 42 of helical screw rheometer (HSR) 44 by bushing 46, tubing connector 48, tubing 50 and tubing connector 52.

Installed in outlet 54 of rheometer 44 is a transducer adapter 56. A pressure transducer 58 is disposed in adapter 56. Outlet 54 has a horizontal leg 60 which is connected to a solenoid valve 62 by a nipple 64. A diode 66 is connected to solenoid valve 62.

A tubing connector 68 is connected to solenoid valve 62, and a tube 70 extends from tubing connector 68 and downwardly into a hole 72 in frame 12. Tube 70 defines a fluid outlet 74 for apparatus 10.

A pair of elbows 76 and 78 are connected to fitting 80 on rheometer 44. A nipple 82 is connected to elbow 78 and is directed downwardly toward hole 72. Elbows 76 and 78 and nipple form an overflow line 83.

Figure 3:
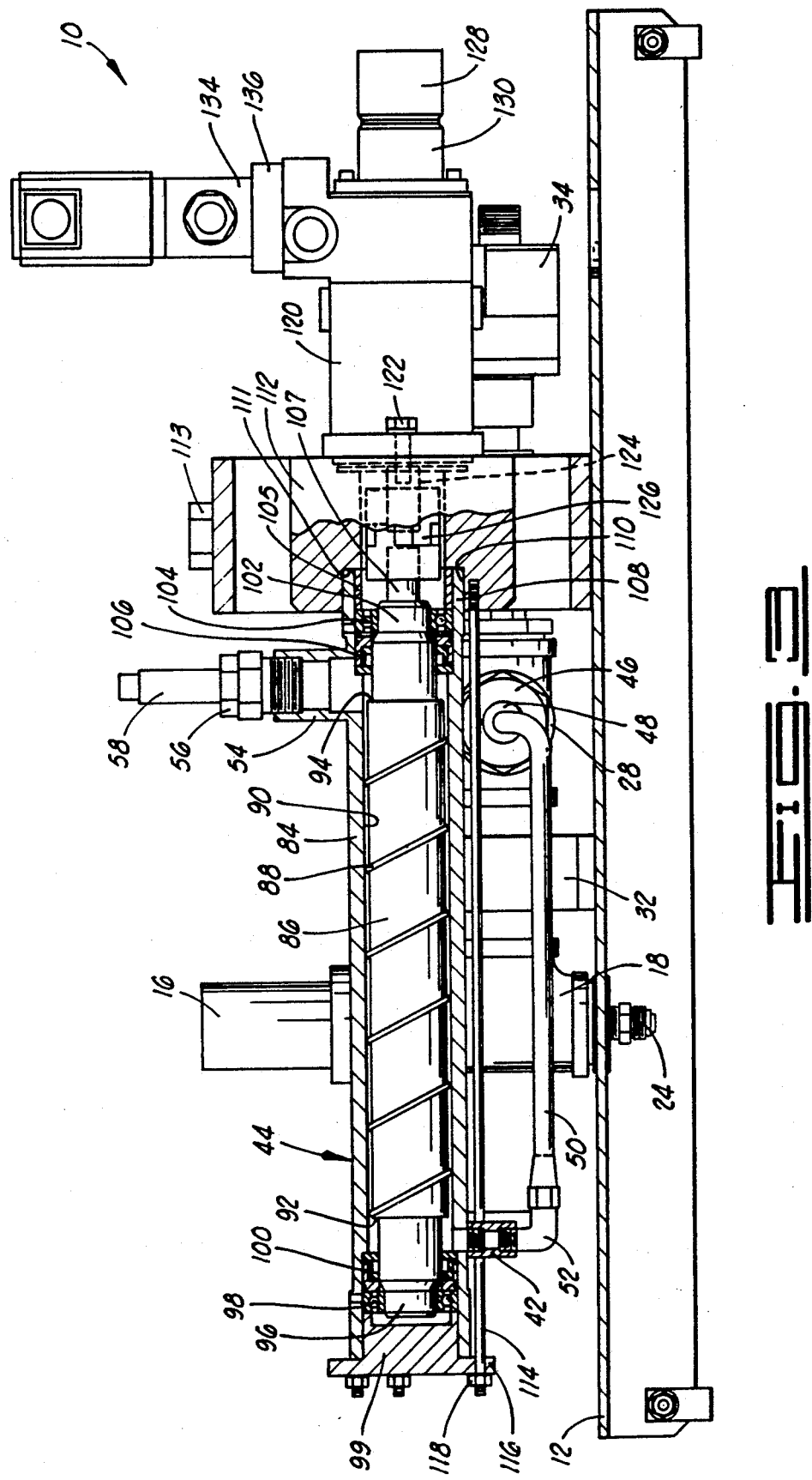
FIG. 3 is a partial cross-sectional and elevational view taken along lines 3—3 in FIG. 1.

Referring now to FIG. 3, the details of rheometer 44 will be discussed. Rheometer 44 generally comprises a housing 84 with a helical screw 86 relatively rotatable therewith. While screw 86 is shown to be rotatably disposed within housing 84, different constructions of the rheometer may be used, and the invention is not intended to be limited to the particular configuration illustrated. For example, rheometers have been built in which the screw is stationary and the outer housing rotates.

Screw 86 has a raised, helical thread portion 88 thereon which is in close relationship with bore 90 in housing 84. Thread 88 extends between a shoulder 92 adjacent to inlet 42 and another shoulder 94 adjacent to outlet 54. It should also be noted that rheometer 44 could be constructed with the thread portion on the inside of housing 84 rather than the external surface of screw 86. Again, various constructions of rheometer 44 are contemplated within the present invention.

Screw 86 has an outboard end 96 which is supported in housing 84 by a bearing 98. An end cap 99 holds bearing 98 in place. A sealing means, such as spring loaded seal 100, provides sealing engagement between screw 86 and housing 84 longitudinally between bearing 98 and shoulder 92.

Screw 86 has a drive end portion 102 which is supported in housing 84 by a bearing 104. A sleeve 105 is positioned adjacent to bearing 104. A sealing means, such as spring loaded seal 106, provides sealing engagement between screw 86 and housing 104 longitudinally between bearing 104 and shoulder 94. A shaft portion 107 extends from drive end portion 102 of screw 86.

A drive end 108 of housing 84 is positioned in bore 110 in housing support 112. Sleeve 105 bears against a shoulder 111 at the end of bore 110, and it will thus be seen that sleeve 105 holds bearing 104 in place on drive end portion 102 of screw 86. Support 112 is attached to frame 12 by fastener means such as bolts 113 and supports rheometer 44 above the frame. A plurality of the bolts 114, characterizing another fastener means, extend through a flange portion 116 of end cap 99 and are threadingly engaged with support 112. A nut 118 is engaged with each tie bolt 114. It will be seen that rheometer 44 is thus held in place with respect to support 112, and end cap 99 is retained on housing 84.

On the opposite side of support 112 from rheometer 44 is a prime mover, such as hydraulic motor 120, which is attached to the support by a fastener means, such as a plurality of bolts 122. Motor 120 has a shaft 124 extending therefrom which is drivingly connected to shaft 107 on screw 86 in rheometer 44 by a coupling 126 of a kind known in the art.

Referring now to FIGS. 1 and 3, an optical encoder 128 is attached to an end of hydraulic motor 120 opposite from shaft 124 by an encoder mount 130 in a manner known in the art. An electrical connector 132 is mounted on optical encoder 128. Optical encoder 128 is adapted to rotate with shaft 124 in motor 120 and transmit a speed signal in response thereto.

A hydraulic proportional valve 134 is attached to an upper side of motor 120 by an adapter 136. Proportional valve 134 is used to control rotation of motor 120 as will be further described herein.

Figure 4:
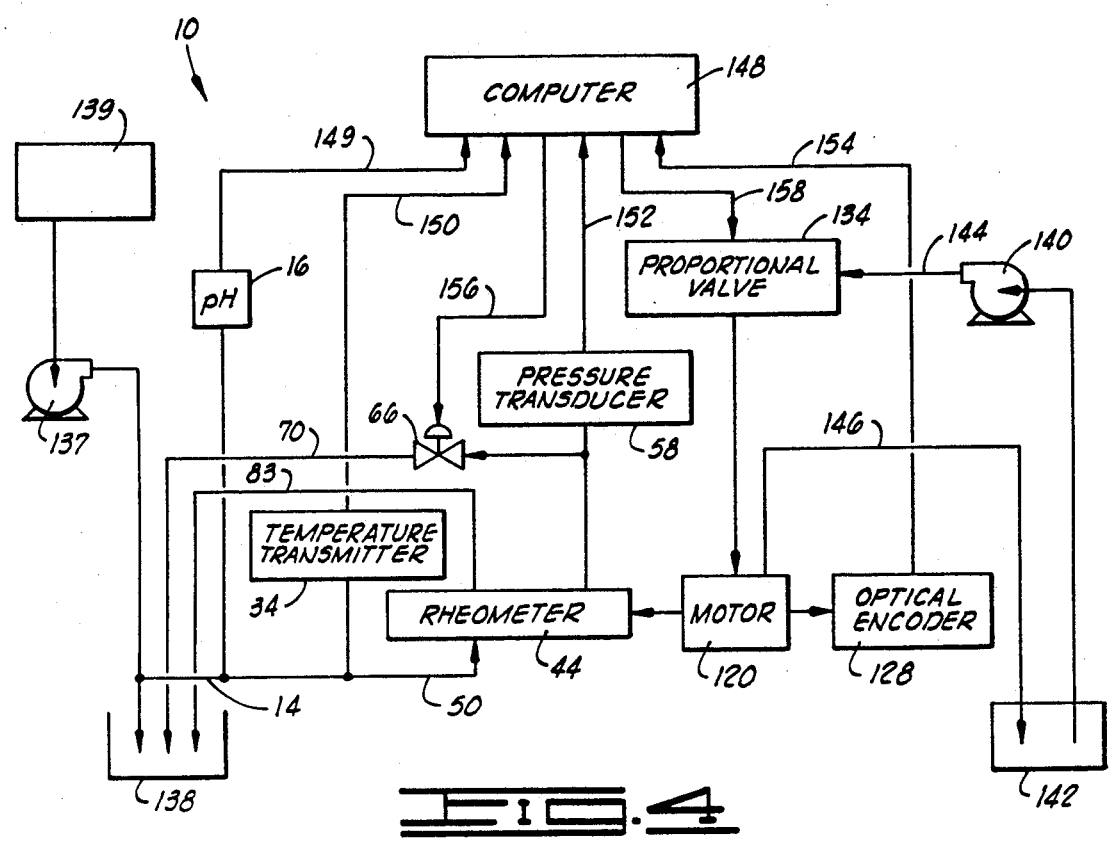
FIG. 4 is a fluid flow and wiring schematic of the present invention device.

Referring now to FIG. 4, a fluid flow and wiring schematic of apparatus 10 is shown. The same numerals indicate those components already described. A pump 173 pumps fluid from a base gel supply tank 139 to a blender tub 138 of a kind known in the art. Pump 137 also supplies fluid to inlet 14 and thus to rheometer 44. Overflow line 83 directs excess fluid back to tub 138. Outlet tube 70 discharges the fluid exiting rheometer 44 back to tub 138.

A pump 140 supplies fluid from a pump reservoir 142 to proportioning valve 134 through line 144. Another line 146 carries fluid from proportional valve 134 back to pump reservoir 142.

Inlet pH sensor 16, temperature transmitter 34, pressure transducer 58, solenoid valve 62, optical encoder 128 and proportional valve 134 are electrically connected to a control means such as a computer means 148. Computer means 148 receives a pH signal 149 from pH sensor 16, temperature signal 150 from temperature transmitter 34, a pressure signal 152 from pressure transducer 58 and a speed or RPM signal 154 from optical encoder 128. Actuating signals 156 and 158 are sent from computer means 148 to solenoid valve 62 and proportional valve 134, respectively.

Operation Of The Invention

Apparatus 10 is used to determine n' and k' parameters of a log of shear rate versus a log of shear stress relationship of the fluid being tested. This relationship is represented by the following equation:

$$\tau = k' \gamma^{n'}$$

Where:
$\tau$ = fluid shear stress
$\gamma$ = fluid shear rate
n' = a parameter represented by the slope of a log-log curve of differential pressure versus speed in RPM
k' = a parameter represented by the unity intercept of that log-log curve Once the n' and k' parameters are known, predictions may be generated for friction pressure loss and bottom hole treating pressure during a fracturing treatment being performed on a well. The parameters may be further used by the computer for correlation to turbulent flow in pipes of various diameters and other information such as quality control of the base gel.

Figure 5:
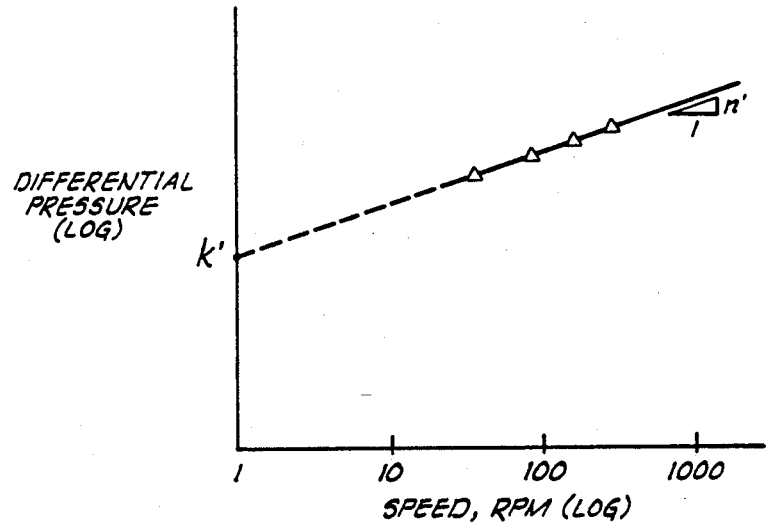
FIG. 5 is a log-log plot of differential pressure versus speed.

As with methods of the prior art, a plurality of sets of differential pressure versus speed data points are obtained and a log-log plot generated such as illustrated in FIG. 5.

In a first embodiment, four sets of data points are used, but this number may be varied if desired. A straight line representation of the data is plotted using a least squares method, and the slope (n') and the unity intercept (k') are calculated.

In the first method, the data points are obtained and the other information is calculated as follows:
A. Fluid is allowed to flow into apparatus 10 from pump 137. In the preferred embodiment, it takes about one minute to fill the system.
B. Pump 140 is energized so that it supplies fluid to proportional valve 134 and thus hydraulic motor 120. Valve 134 is initially set so that the motor speed is at approximately 100 RPM or other preselected substantially constant speed. This can be controlled manually by the operator or automatically through computer means 148 because computer means 148 receives speed signal 154 from optical encoder 128 and can control the position of proportional valve 134 by actuating signal 158. Motor 120, and thus rheometer 44, are rotated for approximately fifteen seconds at 100 RPM with solenoid valve 62 open. This insures that any air in rheometer 44 is cleared out and a good homogeneous mixture of fluid is in the rheometer.
C. The rotation of motor 120 and rheometer 44 is stopped for approximately four seconds, and solenoid valve 62 is closed. Again, this control may be carried out by computer means 148. The static pressure in the system is then measured by pressure transducer 58 and a corresponding pressure signal 152 sent to computer means 148. This pressure is received by the computer means and reset as a "zero" point for comparison with a subsequent pressure signal. As will be seen, this eliminates the need for a differential pressure transducer.
D. Valve 134 is actuated so that motor 120 and rheometer 44 are operated at a first substantially constant speed for six seconds. Solenoid valve 62 remains closed. Screw 86 in rheometer 44 forces fluid from inlet 42 toward outlet 54 thereof. Because solenoid valve 62 is closed, fluid cannot exit rheometer 44, but rather there is internal fluid slippage. A pressure is generated at outlet 54, however, and this pressure is measured by pressure transducer 58 with a corresponding pressure signal 152 sent to computer means 148 for comparison with the previous "zeroed" pressure. At substantially the same time, speed signal 154 is received by computer means 148 from optical encoder 128. Because the pressure was zeroed, the outlet pressure measured is substantially equal to the differential pressure across rheometer 44, and a differential pressure point is thus determined for the first speed.
E. Step D is repeated for three additional speeds.
F. Solenoid valve 62 is opened, and rheometer 44 is rotated at 100 RPM for fifteen seconds to provide fresh fluid thereto. Steps C, D and E may be repeated if desired for additional testing.

After the differential pressure has been determined for the fourth speed, the least squares calculation is carried out by computer means 148, and the slope (n') and unity intercept (k') are determined. The equation for the shear rate versus shear stress relationship of the fluid may then be solved as previously discussed.

In the preferred embodiment of the first method, the operator selects the first and last speeds, such as 50 RPM and 450 RPM. Computer means 148 then calculates the second and third speeds, for example, 104 and 215 RPM. The selection of any or all of the speeds may be done manually, and it i not intended that the invention be limited to these particular speeds or to computer control in general.

During the six-second test of step (d) described above, computer means 148 measures the pressure approximately eight times during the last second of the six-second test to determine an accurate average for the speed selected.

Thus, apparatus 10 may be used to obtain four data points just as was the case with prior art methods. However, a single pressure transducer 58 is used rather than a plurality of differential pressure transducers with their associated complex connections. The results have been shown to be extremely accurate, and this is important in controlling the quality of the base gel during well fracturing treatments.

In a second or alternate embodiment, a plurality of data points are again obtained but the screw in helical screw rheometer 44 is not stopped between data points. As with the first embodiment, however, a straight line representation of the data is plotted using a least squares method, and the slope (n') and the unity intercept (k') are calculated a in the first method.

In this alternate embodiment, the data points are obtained and the other information is calculated as follows:

A. Fluid is allowed to flow into apparatus 10 from pump 137. In the preferred embodiment, it takes about one minute to fill the system.

B. Pump 140 is energized so that it supplies fluid to proportional valve 134 and thus hydraulic motor 120. Valve 134 is initially set so that the motor speed is at some preselected value. As with the first embodiment, this can be controlled manually by the operator or automatically through computer means 148. Typically, motor 120, and thus rheometer 44, are rotated for approximately fifteen seconds with solenoid valve 62 open. This insures that any air in rheometer 44 is cleared out and a good homogeneous mixture of fluid is in the rheometer.

C. The rotation of motor 120 and rheometer 44 is stopped for approximately four seconds, and solenoid valve 62 is closed. Again, this control may be carried out by computer means 148. Static pressure in the system is then measured by pressure transducer 58 and a corresponding pressure signal 152 sent to computer means 148. This pressure is received by the computer means and reset as a "zero point" for comparison with subsequent pressure signals. Again, this eliminates the need for a differential pressure transducer.

D. Valve 134 is actuated so that motor 120 and rheometer 44 are operated with the speed varying over a speed range for a period of time. That is, the helical screw rheometer does not need to be held at a constant speed for a discrete number of steps. Instead, it can be linearly accelerated at an increasing speed and the pressure sampled at substantially the same time as the speed. For example, the speed of the helical screw rheometer may be changed from 50 RPM to 450 RPM over a period of time, for example six seconds, and the pressure and speed sampled or measured at a time interval, for example, 0.5 seconds. The pressures generated at outlet 54 over the speed range are measured by pressure transducer 58 with corresponding pressure signals 152 sent to computer means 148 for comparison with the previous "zeroed" pressure. At substantially the same time, corresponding speed signals 154 are received by computer means 148 from optical encoder 128. Because the initial, static pressure was zeroed, the outlet pressures measured are substantially equal to the differential pressures across rheometer 44 for the corresponding speeds.

After the differential pressures have been determined for the speed intervals over the speed range, the least squares calculation is carried out by computer means 148, and the slope (n') and unity intercept (k') are determined. The equation for the shear rate versus shear stress relationship of the fluid may then be solved as in the first embodiment. Essentially, the plot of the data in this alternate embodiment will appear the same as in FIG. 5 only it will have more data points.

While this alternate embodiment of the method has been cited with a specific speed range and time intervals, it should be understood that the invention is not intended to be limited to these specific values. It is further not intended that the invention be limited to a speed range in which the speed is constantly increasing. Any variation in speed which will generate enough data will be sufficient for obtaining the n' and k' parameters.

It will be seen, therefore, that the rheology test apparatus and method of the present invention are well adapted to carry out the ends and advantages mentioned, as well as those inherent therein. While a presently preferred embodiment of the apparatus and preferred steps in the method have been described for the purposes of this disclosure, numerous changes in the arrangement and construction of parts in the apparatus and variations in the steps of the method may be made by those skilled in the art. All such changes are encompassed within the scope and spirit of the appended claims.

What is claimed is:

1. A rheology test apparatus for use in determining fluid properties of base gels for well fracturing operations, said apparatus comprising:
   a helical screw rheometer comprising:
   a housing having an inlet and an outlet; and
   a screw disposed in said housing;
   wherein, said housing and screw are relatively rotatable;
   a prime mover for providing relative rotation between said housing and screw;
   speed control means for controlling a speed of said prime mover;
   valve means for closing said outlet of said helical screw rheometer;
   pressure sensing means for sensing an outlet pressure of said helical screw rheometer when said outlet is closed and in response to a speed of said prime mover;
   speed sensing means for measuring a speed of said prime mover; and
   computer means for receiving a signal from said pressure sensing means and a signal from said speed sensing means and controlling said speed control means.

2. The apparatus of claim 1 further comprising speed sensing means for measuring a speed of said prime mover.

3. The apparatus of claim 2 further comprising computer means for receiving a signal from said pressure sensing means and a signal from said speed sensing means and controlling said speed controlling means.

4. The apparatus of claim 1 wherein said computer means further comprises means for actuating said valve means for opening and closing said outlet.

5. The apparatus of claim 1 wherein said computer means further comprises means for calculating an intermediate speed during a series of tests in response to preselected first and last speeds.

6. The apparatus of claim 1 wherein said computer means further comprises means for calculating, in response to said pressure sensing means and speed sensing means, n' and k' parameters of a shear rate versus shear stress relationship of a fluid in said helical screw rheometer.

7. The apparatus of claim 1 wherein said valve means is disposed downstream of said pressure sensing means.

8. The apparatus of claim 1 wherein said screw is rotatable within said housing.

9. The apparatus of claim 1 wherein said screw has a substantially helical thread thereon.

10. A method of rheological testing comprising the steps of:
   (a) flowing a fluid into a helical screw rheometer;
   (b) closing an outlet of said helical screw rheometer;
   (c) rotating a screw in said helical screw rheometer at a substantially constant speed for a predetermined time period;
   (d) measuring a differential pressure across said helical screw rheometer;
   (e) repeating steps (c) and (d) for another substantially constant speed of said helical screw rheometer;
   (f) using computer means for calculating, in response to the differential pressure values and speeds, n' and k' parameters of a shear rate versus shear stress relationship of said fluid; and
   (g) using said computer means for selecting an intermediate speed of said helical screw rheometer in a plurality of tests in response to preselected first and last speeds of said tests.

11. A rheology test apparatus for use in determining fluid properties of base gels for well fracturing operations, said apparatus comprising:
   a helical screw rheometer comprising:
   a housing having an inlet and an outlet; and
   a screw disposed in said housing;
   wherein, said housing and screw are relatively rotatable;
   a prime mover for providing relative rotation between said housing and screw;
   speed control means for controlling a speed of said prime mover;
   valve means for closing said outlet of said helical screw rheometer;
   pressure sensing means for sensing an outlet pressure of said helical screw rheometer when said outlet is closed and in response to a speed of said prime mover;
   speed sensing means for measuring a speed of said prime mover; and
   computer means for receiving a signal from a pressure sensing means and a signal from said speed sensing means and controlling said speed controlling means, wherein said compute means further comprises means for resetting a pressure measurement to zero after measuring a static pressure in said helical screw rheometer so that a subsequent measurement of a dynamic pressure in said helical screw rheometer is substantially equal to a differential pressure thereacross.

12. A method of rheological testing comprising the steps of:
   (a) flowing a fluid into a helical screw rheometer;
   (b) closing an outlet of said helical screw rheometer;
   (c) rotating a screw in said helical screw rheometer at a substantially constant speed for a predetermined time period;
   (d) measuring a differential pressure across said helical screw rheometer, said measuring comprising;
   stopping said screw in said helical screw rheometer;
   measuring a pressure at an outlet of said helical screw rheometer to obtain a static pressure value;
   resetting said static pressure value to zero;
   rotating said screw at said constant sped; and
   measuring a pressure at said outlet of said helical screw rheometer to obtain a dynamic pressure value;
   (e) repeating steps (c) and (d) for another substantially constant speed of said helical screw rheometer; and
   (f) calculating, in response to the differential pressure values and speeds, n' and k' parameters of a shear rate versus shear stress relationship of said fluid.

13. The method of claim 12 further comprising using computer means for resetting said static pressure value to zero such that said dynamic pressure value is substantially equal to a differential pressure across said helical screw rheometer.

14. The method of claim 13 further comprising using computer means for carrying out step (f).

15. A method of rheological testing comprising the steps of:
   (a) flowing a fluid into a helical screw rheometer;
   (b) closing an outlet of said helical screw rheometer;
   (c) rotating a screw in said helical screw rheometer and varying the speed thereof over a speed range for a period of time;
   (d) periodically measuring a differential pressure across said helical screw rheometer at different speeds within said speed range, said measuring comprising;
   prior to varying said speed, measuring a pressure at an outlet of said helical screw rheometer with said screw in said helical screw rheometer stopped to obtain a static pressure value;
   resettting said static pressure value to zero;
   rotating said screw over said speed range; and
   periodically measuring a pressure at said outlet of said helical screw rheometer to obtain a series of dynamic pressure values; and
   (e) calculating, in response to the differential pressure values and speeds, n' and k' parameters of a shear rate versus shear stress relationship of said fluid.

16. The method of claim 15 further comprising using computer means for resetting said static pressure value to zero such that said series of dynamic pressure values is substantially equal to a series of differential pressures across said helical screw rheometer for the corresponding speeds in said speed range.

* * * * *